United States Patent
Lakamraju et al.

(10) Patent No.: US 10,746,426 B2
(45) Date of Patent: Aug. 18, 2020

(54) AGENT DETECTION SYSTEM ASSISTED BY A BUILDING SUBSYSTEM

(71) Applicant: Carrier Corporation, Palm Beach Gardens, FL (US)

(72) Inventors: Vijaya Ramaraju Lakamraju, Avon, CT (US); Peter R. Harris, West Hartford, CT (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 102 days.

(21) Appl. No.: 16/060,174

(22) PCT Filed: Dec. 7, 2016

(86) PCT No.: PCT/US2016/065276
§ 371 (c)(1),
(2) Date: Jun. 7, 2018

(87) PCT Pub. No.: WO2017/100253
PCT Pub. Date: Jun. 15, 2017

(65) Prior Publication Data
US 2018/0363935 A1    Dec. 20, 2018

Related U.S. Application Data

(60) Provisional application No. 62/264,499, filed on Dec. 8, 2015.

(51) Int. Cl.
*F24F 11/30* (2018.01)
*G01N 33/00* (2006.01)
(Continued)

(52) U.S. Cl.
CPC .............. *F24F 11/30* (2018.01); *F24F 11/58* (2018.01); *F24F 11/89* (2018.01);
(Continued)

(58) Field of Classification Search
CPC ...... F24F 11/89; F24F 11/58; G01N 33/0075; G05B 15/02
See application file for complete search history.

(56) References Cited

U.S. PATENT DOCUMENTS

| 6,583,726 B1 | 6/2003 | Johnson et al. |
| 6,688,968 B2 | 2/2004 | Krafthefer |

(Continued)

FOREIGN PATENT DOCUMENTS

WO    2007027631 A1    3/2007

OTHER PUBLICATIONS

Cloud Connect—Evolve IP; retrieved from Internet: URL: http://www.evolveip.net/network/cloud-connect; © 2015Evolve IP, LLC; 2 pgs.

(Continued)

*Primary Examiner* — Ronald D Hartman, Jr.
(74) *Attorney, Agent, or Firm* — Cantor Colburn LLP

(57) ABSTRACT

An indoor air quality monitoring system (20) is adapted to function within a space (26) utilizing a building subsystem (22), such as a heating ventilation air conditioning (HVAC) unit, configured to control an ambient parameter, such as temperature, humidity or lightning, in the space (26). The system (20) includes an agent detector (30) configured to detect an agent in ambient air, such as smoke, biohazards or particulate matter, and sequentially output an initial agent measurement signal and a subsequent agent measurement signal. A controller (34) of the system (20) includes a processor and a storage media. The controller (34) is pre-programmed with an agent threshold value, and configured to receive the initial agent measurement signal, compare the signal to the agent threshold value, and if the signal exceeds the agent threshold value, then send a command signal (42) to the subsystem (22) to alter the ambient parameter asso- (Continued)

ciated with the agent detector, and then receive the subsequent agent measurement signal from the agent detector associated with the altered ambient parameter.

20 Claims, 2 Drawing Sheets

(51) Int. Cl.
  *F24F 11/89*   (2018.01)
  *F24F 11/58*   (2018.01)
  *G05B 15/02*   (2006.01)
  *F24F 110/50*   (2018.01)
  *F24F 110/10*   (2018.01)
  *F24F 110/65*   (2018.01)

(52) U.S. Cl.
  CPC ......... *G01N 33/0075* (2013.01); *G05B 15/02* (2013.01); *F24F 2110/10* (2018.01); *F24F 2110/50* (2018.01); *F24F 2110/65* (2018.01); *F24F 2203/00* (2013.01)

(56) References Cited

U.S. PATENT DOCUMENTS

| | | |
|---|---|---|
| 6,701,772 B2 | 3/2004 | Kreichauf et al. |
| 6,834,533 B2 | 12/2004 | Megerle |
| 7,096,125 B2 | 8/2006 | Padmanabhan et al. |
| 7,561,264 B2 | 7/2009 | Treado et al. |
| 7,578,973 B2 | 8/2009 | Call et al. |
| 7,765,072 B2 | 7/2010 | Eiler et al. |
| 7,916,015 B1 | 3/2011 | Evancich et al. |
| 8,545,761 B2 | 10/2013 | Cox |
| 9,103,805 B2 | 8/2015 | Gettings et al. |
| 2002/0155807 A1* | 10/2002 | Moor ............... F24F 7/007 454/342 |
| 2003/0114986 A1 | 6/2003 | Padmanabhan et al. |
| 2004/0186339 A1* | 9/2004 | Galloway ............ A61L 9/16 588/316 |
| 2008/0182506 A1 | 7/2008 | Jackson et al. |
| 2008/0262321 A1 | 10/2008 | Erad et al. |
| 2008/0273572 A1 | 11/2008 | Lawrence et al. |
| 2009/0009345 A1* | 1/2009 | Conforti ............ G08B 17/107 340/627 |
| 2009/0055102 A1* | 2/2009 | Laufer ............ G01N 1/2273 702/24 |
| 2011/0236267 A1* | 9/2011 | Cox ............ G01N 33/0031 422/93 |
| 2013/0309154 A1* | 11/2013 | Call ............ G08B 21/12 423/210 |
| 2014/0075011 A1 | 3/2014 | Salkintzis |
| 2014/0238107 A1 | 8/2014 | Chou et al. |
| 2014/0334653 A1* | 11/2014 | Luna ............ G05B 15/02 381/332 |
| 2015/0156679 A1 | 6/2015 | Li et al. |

OTHER PUBLICATIONS

International Search Report from the International Searchign Authority for International Application No. PCT/US2016/065276; Date of Completion: Feb. 23, 2017; dated Mar. 6, 2017; 6 Pages.

Written Opinion from the International Searching Authority for International Application No. PCT/US2016/065276; International Filing Date: Dec. 7, 2016; dated Mar. 6, 2017; 6 Pages.

\* cited by examiner

US 10,746,426 B2

AGENT DETECTION SYSTEM ASSISTED BY A BUILDING SUBSYSTEM

CROSS REFERENCE TO RELATED APPLICATIONS

This application is a National Stage application of PCT/US2016/065276, filed Dec. 7, 2016, which claims the benefit of U.S. Provisional Application No. 62/264,499, filed Dec. 8, 2015, both of which are incorporated by reference in their entirety herein.

BACKGROUND

The present disclosure relates to an agent detection system and, more particularly, to an agent detection system utilizing a building subsystem to enable faster detection and more accurate confirmation of the measurement of the agent.

Cost effective, harmful, agent detection in buildings continues to gain prominence. One method of achieving cost effective and early detection of agents is accomplished through the use of sensors that may cover a wide area, such as atriums and hallways within the building and the use of multi-role devices (e.g., smoke and bio-agent). Laser based technology such as light distance and ranging (LIDAR) may be viewed as a preferred method to provide such coverage. LIDAR and other agent detection technologies often produce false alarms, and/or delayed alarms. Improvements in agent detection is desirable while maintaining cost effectiveness.

SUMMARY

The foregoing features and elements may be combined in various combinations without exclusivity, unless expressly indicated otherwise. These features and elements as well as the operation thereof will become more apparent in light of the following description and the accompanying drawings. However, it should be understood that the following description and drawings are intended to be exemplary in nature and non-limiting.

An agent detection system for a building utilizing a building subsystem configured to control an ambient parameter in the building, the agent detection system including at least one agent detector configured to detect an agent in ambient air and sequentially output an initial agent measurement signal and a subsequent agent measurement signal; and a controller including a computer processor and a computer readable storage media, the controller being preprogrammed with at least one agent threshold value, and configured to receive the initial agent measurement signal, compare the initial agent measurement signal to the at least one agent threshold value, and if the initial agent measurement signal exceeds the at least one agent threshold value then send a command signal to the air handler unit to alter the ambient parameter associated with the at least one agent detector and receive the subsequent agent measurement signal associated with the altered ambient parameter.

Additionally to the foregoing embodiment, the subsequent agent measurement signal comprises an agent not detected signal and a confirmed agent detected signal.

In the alternative or additionally thereto, in the foregoing embodiment, the controller is configured to compare the subsequent agent measurement signal to the at least one agent threshold value and initiate an agent detected action if the subsequent agent measurement signal exceeds the at least one agent threshold value.

In the alternative or additionally thereto, in the foregoing embodiment, the building subsystem is an air handler unit and the ambient parameter is at least one of air temperature and air humidity.

In the alternative or additionally thereto, in the foregoing embodiment, the building subsystem is a lighting system and the ambient parameter is light intensity.

In the alternative or additionally thereto, in the foregoing embodiment, the building subsystem is an air handler unit and the ambient parameter is airflow volume.

In the alternative or additionally thereto, in the foregoing embodiment, the at least one agent detector comprises a first agent detector for outputting the initial agent measurement signal and a second agent detector for outputting the subsequent agent measurement signal.

In the alternative or additionally thereto, in the foregoing embodiment, the first agent detector is disposed in a first location of the building having a first segment of the ambient air and the second agent detector is located in a second location of the building having a second segment of the ambient air.

In the alternative or additionally thereto, in the foregoing embodiment, the building subsystem is a heating, ventilation and air conditioning system including a variable air volume box controlled at least in-part by the controller.

In the alternative or additionally thereto, in the foregoing embodiment, the at least one agent detector comprises a smoke detector.

In the alternative or additionally thereto, in the foregoing embodiment, the at least one agent detector comprises a chemical detector.

In the alternative or additionally thereto, in the foregoing embodiment, the at least one agent detector includes an infrared light source and the ambient parameter is air temperature.

In the alternative or additionally thereto, in the foregoing embodiment, the at least one agent detector comprises a biological detector.

In the alternative or additionally thereto, in the foregoing embodiment, the at least one agent detector includes an ultraviolet light source and the ambient parameter is air temperature.

In the alternative or additionally thereto, in the foregoing embodiment, the at least one agent detector includes a wide field of view associated with the initial agent measurement signal, and a narrow field of view associated with the subsequent agent measurement signal.

In the alternative or additionally thereto, in the foregoing embodiment, the at least one agent detector is a multi-role detector.

A method of detecting an agent in ambient air according to another, non-limiting, embodiment includes measuring the ambient air for the presence of the agent by at least one detector; sending an initial agent measurement signal from the at least one detector to a controller; confirming the initial agent measurement signal exceeds at least one agent threshold value by the controller; sending a command signal to an air handler unit to alter an ambient parameter associated with the ambient air by the air handler unit; measuring the ambient air for the presence of the agent by at least one detector; sending a subsequent agent measurement signal from the at least one detector to the controller; confirming the subsequent agent measurement signal exceeds at least one agent threshold value by the controller; and outputting an action by the controller.

Additionally to the foregoing embodiment, the at least one detector is a first detector and the ambient parameter is a change in airflow pattern proximate to the first detector.

In the alternative or additionally thereto, in the foregoing embodiment, a first detector located in a first space portion outputs the initial agent measurement signal, a second detector located in a second space portion outputs the subsequent agent measurement signal, and the altered ambient parameter is a transfer of air volume from the first space portion to the second space portion.

In the alternative or additionally thereto, in the foregoing embodiment, the altered ambient parameter is a change in temperature.

The foregoing features and elements may be combined in various combinations without exclusivity, unless expressly indicated otherwise. These features and elements as well as the operation thereof will become more apparent in light of the following description and the accompanying drawings. However, it should be understood that the following description and drawings are intended to be exemplary in nature and non-limiting.

BRIEF DESCRIPTION OF THE DRAWINGS

Various features will become apparent to those skilled in the art from the following detailed description of the disclosed non-limiting embodiments. The drawings that accompany the detailed description can be briefly described as follows.

DETAILED DESCRIPTION

Figure 1:
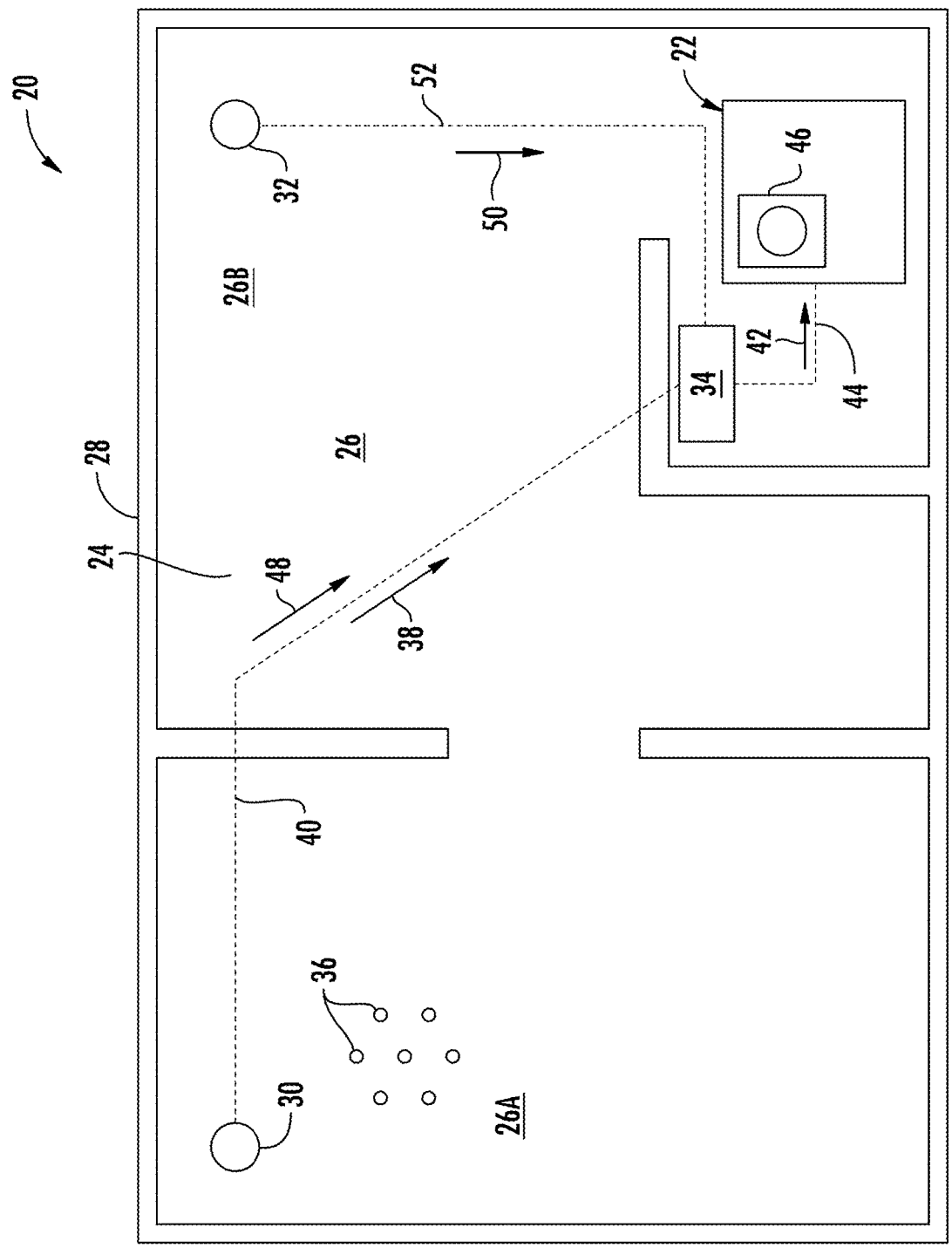
FIG. 1 is a schematic of a building utilizing an agent detection system as one, non-limiting, exemplary embodiment of the present disclosure.

Referring to FIG. 1, an exemplary embodiment of an agent detection system 20 assisted by a subsystem 22 of, for example, a building. Examples of a building subsystem 22 may include a utility system such as an air handler unit (as illustrated), a lighting system, and others. The agent detection system 20 facilitates the detection of an agent in ambient air 24 that generally fills a defined space 26. The space 26 may be defined by a structure 28 that may, for example, be an occupied building. The primary function of the building subsystem 22, as an air handler unit, may facilitate conditioning of the ambient air 24 in the building 28 and/or space 26 toward, for example, the comfort of the building occupants. Non-limiting examples of an air handler unit 22 may include a heating and ventilation air condition (HVAC) system that may be designed to control temperature, humidity, filtration and air volume flow of the ambient air 24, or, a hydronic heating system that may be designed to control the temperature of the ambient air 24, without, necessarily, the movement of air through the space 26. Further non-limiting control includes the control of lighting in a space. Non-limiting examples of agents may include particulate and/or smoke, chemical agents and biological agents.

The agent detection system 20 may include a first agent detector 30 disposed in a first portion 26A of the space 26, a second agent detector 32 that may be disposed in a different, second, portion 26B of the space 26, and a controller 34 that may include a computer processor (e.g., microprocessor) and a computer readable storage media. The controller 34 may, for example, be part of a building management system, and/or may be comprised of a plurality of controllers. The plurality of controllers may be decentralized and/or may be integrated, at least in-part, into the agent detectors 30, 32. It is further contemplated and understood that the agent detector 30 may be present by itself (i.e., no detector 32) and is sufficiently sophisticated to detect any changes.

In one embodiment, the first agent detector 30 may be configured to monitor the ambient air 24 in space portion 26A for the presence of an agent 36 that may be airborne. The first agent detector 30 may be further configured to measure the concentration of the agent 36 and output an initial agent measurement signal (see arrow 38) to the controller 34 over a pathway 40 that may be wired or wireless. The controller 34 is configured to receive the initial agent measurement signal 38, process the signal, and compare the associated initial agent measurement concentration to a pre-programmed agent threshold value.

If the controller 34 determines that the initial agent measurement concentration associated with the initial agent measurement signal 38 is less than the agent threshold value, the controller 34 may do nothing and the first agent detector 30 will continue to monitor the space portion 26A as before. If the controller 34 determines that the initial agent measurement concentration is greater than the agent threshold value, the controller 34 will take action to confirm that the agent 36 is accurately detected.

To confirm accurate detection of the agent 36, the controller 34 may initiate a command signal (see arrow 42) to the air handler unit 22 over a pathway 44 that may be wired or wireless. The command signal 42 may cause the air handler unit 22 to change an air parameter in a pre-designated area (i.e., one of the space portions 26A, 26B or others). In one example, the command signal 42 may cause for example, a variable air volume (VAV) box 46 of the air handler unit 22 to change the airflow pattern or volume in space portion 26A proximate to the agent detector 30 that detected the initial agent presence. In this example, the same detector will continue to monitor the ambient air 24 now having a differing air parameter (e.g., airflow pattern, temperature, humidity). If a subsequent agent measurement signal (see arrow 48) sent from the first agent detector 30 to the controller 34 generally exceeds the agent threshold value (or a second pre-programmed agent threshold), then the controller has confirmed the presence of the agent 36 in space portion 26A. Upon this confirmation, the controller 34 may take any variety of actions appropriate for the given condition.

In another agent detection scenario and after an agent 36 is initially detected by the detector 30 in space portion 26A, the command signal 42 may cause the air handler unit 22 to divert a portion of the ambient air 24 from space portion 26A and into space portion 26B for a confirmation measurement by agent detector 32 to increase detection confidence levels through redundancy. If a subsequent agent measurement signal (see arrow 50) sent from the second agent detector 32 to the controller 34 over pathway 52 generally exceeds the agent threshold value, then the controller has confirmed the accuracy of detector 30 and the presence of the agent 36 in space portion 26A. Upon this confirmation, the controller 34 may take any variety of actions appropriate for the given condition. If the second detector 32 fails to detect the agent (i.e. sufficient concentration levels) then the controller 34 may do nothing or may provide a notification that the first detector 30, for example, may require maintenance. It is further contemplated and understood that in this example, the detectors 30, 32 may be of different types. It is also understood that the first detector 30 may have a wide angle of view and the second detector 32 may have a smaller and more accurate angle of view that targets the specific airflow (i.e. sample) re-routed and provided by the air handler unit 22.

It is contemplated and understood that what the air handler unit 22 is commanded to do (i.e. air parameter changes and in what space portions) is dependent upon the agent being detected and the type of detector being used. The agent detector types may include, but are not limited to, conventional smoke detectors, detectors having an ultraviolet light source, detectors that have an infrared light source that may apply a fourier transform infrared spectrometry technology, and other detectors that may include multi-roles. It is further contemplated and understood that the first agent detector may not be the same type as the second agent detector. Moreover, the second agent detector may not be required at all to confirm the first detector measurement, or there may be many detectors with at least one detector located internal to the air handler unit 22.

In another embodiment, one or both of the initial and subsequent agent measurement signals 38, 50 sent to the controller may not be actual measurement values and, instead, may be simple agent detected or agent not detected signals. In such an example, any agent threshold values may be pre-defined or pre-programmed into the detector(s) itself.

In one embodiment, the agent 36 may be a particulate or a biological agent and at least one of the detectors 30, 32 may include an ultraviolet light source. In this example, the air parameter that is changed may be air temperature that results in a detectable fluorescence change of, for example, biological molecules.

In another embodiment, the agent 36 may be a chemical agent and at least of the detectors 30, 32 may include an infrared light source. The air parameter that is changed may be air temperature which in-turn changes a spectrum of a particular species when, for example, a fourier transform infrared spectrometry technology is applied. It is contemplated and understood that apart from air flow and temperature, ambient lighting may be changed as a parameter that may have an impact on the detectability of an agent. More specifically and a one non-limiting example, for incandescent and some LED lights, infrared energy may, in-part, be radiated. For example, a one-hundred Watt incandescent bulb may produce about twelve percent heat, eighty-three percent infrared energy and about five percent visible light. Therefore, an infrared detector or sensor may be used in conjunction with a lighting system to detect, for example, a chemical in the ambient air that is illuminated.

It is further contemplated and understood that the detectors 30, 32, the air handler unit 22 and the controller 34 may all, or in-part, be part of pre-existing equipment. Furthermore, the controller 34 may be part of a pre-existing building management system such that implementing the present disclosure may involve little more than programming a pre-existing processor of a pre-existing building management system to implement the agent detection and confirmation method described herein. The present disclosure may utilizing pre-existing components but in different applications and/or different combinations to perform differing tasks.

Figure 2:
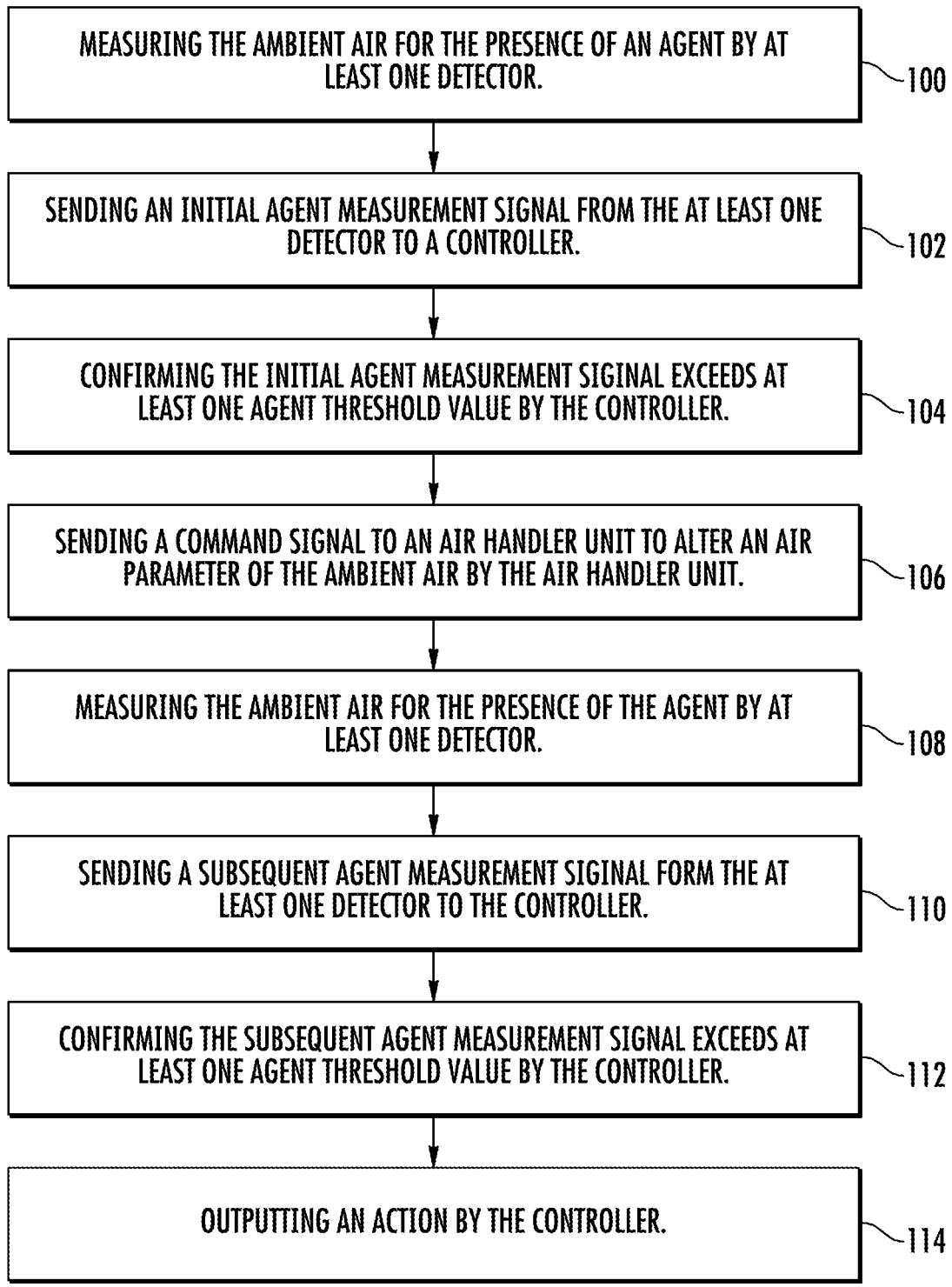
FIG. 2 is a flow chart illustrating a method of operating the agent detection system.

Referring to FIG. 2, a method of operating the agent detection system 20 may include a first step 100 of measuring the ambient air 24 for the presence of the agent 36 by at least one detector 30, 32. A next step 102 may include sending an initial agent measurement signal 38 from the at least one detector 30, 32 to a controller 34. A next step 104 may include confirming the initial agent measurement signal 38 exceeds at least one agent threshold value by the controller 34. A next step 106 may include sending a command signal 42 to an air handler unit 22 to alter an air parameter of the ambient air 24 by the air handler unit 22. A next step 108 may include measuring the ambient air 24 for the presence of the agent 36 by at least one detector 30, 32. A next step 110 may include sending a subsequent agent measurement signal 48, 50 from the at least one detector 30, 32 to the controller 34. A next step 112 may include confirming the subsequent agent measurement signal 48, 50 exceeds at least one agent threshold value by the controller 34. A next step 114 may include outputting an action by the controller 34.

While the present disclosure is described with reference to exemplary embodiments, it will be understood by those skilled in the art that various changes may be made and equivalents may be substituted without departing from the scope of the present disclosure. In addition, various modifications may be applied to adapt the teachings of the present disclosure to particular situations, applications, and/or materials, without departing from the essential scope thereof. The present disclosure is thus not limited to the particular examples disclosed herein, but includes all embodiments falling within the scope of the appended claims.

What is claimed is:

1. An agent detection system for a building utilizing a building subsystem configured to control an ambient parameter in the building, the agent detection system comprising:
   at least one agent detector configured to detect an agent in ambient air and sequentially output an initial agent measurement signal and a subsequent agent measurement signal configured to confirm the initial agent measurement signal; and
   a controller including a computer processor and a computer readable storage media, the controller being preprogrammed with at least one agent threshold value, and configured to receive the initial agent measurement signal, compare the initial agent measurement signal to a specified one of the at least one agent threshold value, and if the initial agent measurement signal exceeds the specified one of the at least one agent threshold value then send a command signal to the building sub-system to alter the ambient parameter associated with the at least one agent detector and receive the subsequent agent measurement signal associated with the altered ambient parameter to confirm accuracy of the initial agent measurement signal.

2. The agent detection system set forth in claim 1, wherein the subsequent agent measurement signal comprises an agent not detected signal and a confirmed agent detected signal.

3. The agent detection system set forth in claim 1, wherein the controller is configured to compare the subsequent agent measurement signal to the at least one agent threshold value and initiate an agent detected action if the subsequent agent measurement signal exceeds the at least one agent threshold value.

4. The agent detection system set forth in claim 1, wherein the building subsystem is an air handler unit and the ambient parameter is at least one of air temperature and air humidity.

5. The agent detection system set forth in claim 1, wherein the building subsystem is a lighting system and the ambient parameter is light intensity.

6. The agent detection system set forth in claim 1, wherein the building subsystem is an air handler unit and the ambient parameter is airflow volume.

7. The agent detection system set forth in claim 1, wherein the at least one agent detector comprises a first agent detector for outputting the initial agent measurement signal and a second agent detector for outputting the subsequent agent measurement signal.

8. The agent detection system set forth in claim 7, wherein the first agent detector is disposed in a first location of the building having a first segment of the ambient air and the second agent detector is located in a second location of the building having a second segment of the ambient air, and wherein the ambient parameter is altered by flowing ambient air proximate to the first agent detector to the second agent detector prior to outputting the subsequent agent measurement signal.

9. The agent detection system set forth in claim 1, wherein the building subsystem is a heating, ventilation and air conditioning system including a variable air volume box controlled at least in-part by the controller.

10. The agent detection system set forth in claim 1, wherein the at least one agent detector comprises a smoke detector.

11. The agent detection system set forth in claim 1, wherein the at least one agent detector comprises a chemical detector.

12. The agent detection system set forth in claim 11, wherein the at least one agent detector includes an infrared light source and the ambient parameter is air temperature.

13. The agent detection system set forth in claim 1, wherein the at least one agent detector comprises a biological detector.

14. The agent detection system set forth in claim 13, wherein the at least one agent detector includes an ultraviolet light source and the ambient parameter is air temperature.

15. The agent detection system set forth in claim 1, wherein the at least one agent detector includes a wide field of view associated with the initial agent measurement signal, and a narrow field of view associated with the subsequent agent measurement signal.

16. The agent detection system set forth in claim 1, wherein the at least one agent detector is a multi-role detector.

17. A method of detecting an agent in ambient air comprising:

measuring the ambient air for the presence of the agent by at least one detector;

sending an initial agent measurement signal from the at least one detector to a controller;

confirming the initial agent measurement signal exceeds at least one agent threshold value by the controller;

sending a command signal to an air handler unit to alter an ambient parameter associated with the ambient air by the air handler unit;

measuring the ambient air for the presence of the agent by at least one detector;

sending a subsequent agent measurement signal configured to confirm the initial agent measurement signal, and from the at least one detector to the controller;

confirming the subsequent agent measurement signal exceeds at least one agent threshold value by the controller; and outputting an action by the controller.

18. The method set forth in claim 17, wherein the at least one detector is a first detector and the ambient parameter is a change in airflow pattern proximate to the first detector.

19. The method set forth in claim 17, wherein a first detector located in a first space portion outputs the initial agent measurement signal, a second detector located in a second space portion outputs the subsequent agent measurement signal, and the altered ambient parameter is a transfer of air volume from the first space portion to the second space portion.

20. The method set forth in claim 17, wherein the altered ambient parameter is a change in temperature.

* * * * *